United States Patent [19]

Tai

[11] Patent Number: 5,206,150
[45] Date of Patent: Apr. 27, 1993

[54] COMPOSITION OF, METHOD OF PRODUCING AND METHOD OF USING A STABILIZED FORMULATION FOR ASSAYING PEROXIDASE ACTIVITY

[75] Inventor: Hsin-Hsiung Tai, Lexington, Ky.

[73] Assignee: University of Kentucky Research Foundation, Lexington, Ky.

[21] Appl. No.: 604,590

[22] Filed: Oct. 26, 1990

[51] Int. Cl.$^5$ .......................... C12Q 1/28; C12N 9/96
[52] U.S. Cl. ...................................... 435/28; 435/188; 435/963; 436/826; 436/904
[58] Field of Search .......................... 435/28, 188, 963; 436/826, 904

[56] References Cited

U.S. PATENT DOCUMENTS 4,849,342  7/1989  Ben-Michael ........................... 435/28
4,868,108  9/1989  Bahar et al. ............................. 435/28
4,891,314  1/1990  Pauly et al. ............................. 435/28

FOREIGN PATENT DOCUMENTS 1-101899  4/1989  Japan .

OTHER PUBLICATIONS

Parham et al., *Chemical Abstract*, vol. 104, Ref. No. 221656m, 1986.

Primary Examiner—Johnnie R. Brown
Assistant Examiner—Abdel A. Mohamed
Attorney, Agent, or Firm—King & Schickli

[57] ABSTRACT

A formulation for use in detecting and/or determining peroxidase activity comprises a mixture in solution of tetramethylbenzidine, hydrogen peroxide, a buffering agent and bacitracin as a stabilizing agent. The formulation is used as a peroxidase substrate that is stable in solution for an extended period of time and provides enhanced color sensitivity.

22 Claims, No Drawings

COMPOSITION OF, METHOD OF PRODUCING AND METHOD OF USING A STABILIZED FORMULATION FOR ASSAYING PEROXIDASE ACTIVITY

TECHNICAL FIELD

The present invention relates generally to assaying peroxidase activity and more particularly to a stabilized formulation for use in such activity and a method of making the formulation.

BACKGROUND OF THE INVENTION

Many assay procedures utilize enzymes as catalysts for analytical reactions. In particular, the enzyme peroxidase is among the most commonly used in enzymatic detection reactions.

Peroxidases are widespread in nature, being found particularly in a variety of plants. They appear to catalyze the same reaction, but differ markedly in physicochemical and kinetic properties. Three main types of peroxidases have been identified: acidic peroxidases with very high carbohydrate content; neutral or slightly basic peroxidases of medium sugar content; and very basic peroxidases of low sugar content. Among these peroxidases, the C isozyme of horseradish peroxidase is most commonly encountered in biotechnology.

Horseradish peroxidase is popularly used in labeling haptens, antibodies, protein A/G, avidin/streptavidin and DNA for enzyme immunoassay, immunocytochemistry, immunoblot and DNA detection. Detection of enzyme activity in the assay procedures takes advantage of the reactive cooperation between the enzyme and a highly sensitive color-forming agent or chromatic compound. The chromatic compound is a hydrogen donor that changes color due to the loss of hydrogen atoms. The dehydrogenation occurs in the presence of an oxidizing agent, typically hydrogen peroxide ($H_2O_2$). It is this oxidation reaction that is catalyzed by the peroxidase. Since a colored product results from the reaction catalyzed by the enzyme, the peroxidase activity is determined from the intensity of the color generated.

Thus, in a typical assay protocol, the peroxidase is first introduced to the test medium. Then the chromatic compound and $H_2O_2$ are mixed to form a colorless substrate that is added to the medium to test for the enzyme. The chromatic compound as substrate undergoes an oxidation reaction when catalyzed by peroxidase in the presence of $H_2O_2$. A colored product results from the removal of hydrogen from the chromatic compound. The colored product is easily measured by spectrophotometry.

Many different types of chromatic compounds have been used in peroxidase assay procedures. When choosing a chromatic compound to be used in combination with $H_2O_2$ as a peroxidase substrate, it is desired that there be a high rate of oxidation and thus a high rate of color conversion. It is further desired that the product have a stable color for easy spectrophotometric measurement. Examples of known chromatic compounds suitable as hydrogen donors are o-dianisidine, guaiacol, 5-aminosalicylic acid, 2,2'-azino-di-(3-ethyl-benzthiazoline-6-sulfonate) (ABTS), o-phenylenediamine (OPD) and 1,2-benzenediamine. These chromatic compounds have certain disadvantages such as high basal oxidation or poor stability of oxidized product or are mutagenic. Accordingly, an alternative chromatic compound that overcomes these disadvantages is preferred.

One group of chromatic compounds found to overcome the disadvantages described above is of the benzidine type, particularly tetraalkybenzidine or salts thereof. The most successfully used compound of this type is 3,3',5,5'-tetramethylbenzidine (TMB). This compound was synthesized in 1974 and found to have sufficient color sensitivity for use in peroxidase assays and in addition has been shown to desirably be noncarcinogenic (Garner et al., Cancer Letters 1, 39–42 (1975); Garner et al., J. Forensic Sci. 21, 816–821 (1976)). These qualities have popularized TMB to become the chromatic compound of choice for use as a substrate for peroxidase assay (Bos et al , J. Immunoassay 2, 187–204 (1981)).

While TMB provides many desirable qualities for use as a chromatic compound, it has the disadvantage of low stability. Hydrogen peroxide has also long been known to be relatively unstable in solution. Accordingly, early use of the reagents as a combined substrate involved mixing them together at the time of the procedure and then introducing the combination to the test medium. Such a procedure is relatively inconvenient and has been known to lead to inadvertent mixing errors that directly result in incorrect test results.

Artisans have tried in the past to produce a combined chromatic compound/peroxide substrate in advance of the test procedure but the same low stability of the substrate mixture was found. More particularly, when the TMB and $H_2O_2$ cannot coexist as a substrate formulation for extended periods of time. This is because of the spontaneous evolution of color occurring due to the decomposition of the peroxide to give oxygen radicals, that attract hydrogen atoms from the chromatic compound. This occurs even in the absence of a catalyst such as peroxidase. Thus the substrate solution becomes useless in a relatively short time period.

Attempts have been made to find a stabilizing agent that prevents the substrate solution containing both a chromatic compound and peroxide from deteriorating when prepared and stored in a single container. One such attempt is disclosed in U.S. Pat. No. 4,891,314 to Pauly et al. The stabilizing agent utilized in the Pauly formulation is penicillin. While the formulation including the penicillin showed improvement over the prior art by providing some stabilization of the substrate formulation, it is not without its drawbacks and limitations. More particularly, it is disclosed that the addition of penicillin provides only a relatively limited increase in stability for one to several weeks. It has also been found that color sensitivity can be improved over the formulation using penicillin as the stabilizing agent.

Thus a need is identified to find a formulation for use as a substrate for assaying peroxidase activity that contains a chromatic compound, peroxide and a stabilizing agent that provides increased stabilization and color sensitivity. The present invention is shown to satisfy that need.

SUMMARY OF THE INVENTION

Accordingly, it is a primary object of the present invention to provide a formulation for use as a substrate for assaying peroxidase activity that overcomes the drawbacks and disadvantages of the prior art.

Another object of the present invention is to provide a stabilized chromatic compound/peroxide formulation for use as a substrate in assaying peroxidase activity that saves storage space by eliminating the need to maintain separate containers of the individual reagents.

It is a further object of the present invention to provide a chromatic compound/peroxide formulation for use as a substrate in assaying peroxidase activity which eliminates the need to mix the individual reagents at the time of the test procedure and hence is more convenient to use.

It is an additional object of the present invention to provide a combined chromatic compound/peroxide formulation for use in assaying peroxidase activity that exhibits significantly improved stability.

Another object of the present invention is to provide a chromatic compound/peroxide formulation for use as a substrate in assaying peroxidase activity that provides enhanced detection sensitivity.

It is still a further object of the present invention is to provide a chromatic compound/peroxide formulation for use as a substrate in assaying peroxidase activity that provides longer storage life than is available with prior art formulations.

Other objects and advantages of the present invention will become apparent as the description thereof proceeds.

In satisfaction of the foregoing objects and advantages, there is provided by this invention a formulation for use as a substrate in assaying peroxidase activity including a chromatic compound, a peroxide and a stabilizing agent selected from a group including bacitracin, its precursor, bacitracin components derived by hydrolysis or any mixtures thereof. The use of bacitracin or its family as a stabilizing agent allows the substrate solution to be prepared in advance of the assay procedures and stored for months without deterioration of the reactive components.

The chromatic compound used in the inventive substrate formulation is selected from a group consisting of tetraalkylbenzidine, salts of tetraalkylbenzidine or any mixtures thereof. The preferred substrate is 3,3',5,5'-tetramethylbenzidine (TMB).

The TMB is dissolved in a water-miscible organic solvent to form a first solution. Examples of solvents suitable for use include dimethyl sulfoxide (DMSO), dimethyl formamide, dioxane or tetrahydrofuran. The TMB is most commonly dissolved in DMSO.

A second solution including the stabilizing agent is prepared to mix with the first solution to form the final formulation. An aqueous buffer solution is prepared utilizing an acidic buffer substance. Such buffers as citrate, acetate and phosphate may be employed as the buffer substance. The buffer is utilized to adjust the pH of the final formulation to the optimum level for storage and use.

The stabilizing agent in the form of a bacitracin compound is added to the aqueous buffer solution. It is commonly known in the art that bacitracin is a peptide chain including a series of amino acids. A bacitracin precursor, i.e. a longer peptide chain including the basic bacitracin constituents, may also be utilized. The use of bacitracin components, i.e. The parent bacitracin peptide chain broken down into smaller peptide chains by hydrolysis, is also suggested.

A peroxide either in liquid or solid form is added to the aqueous buffer solution including the stabilizing agent. Typically, hydrogen peroxide or, alternatively, urea hydrogen peroxide is used as the liquid or solid peroxide, respectively. The TMB solution and the peroxide/bacitracin solution, made at room temperature, are then thoroughly mixed together and stored in an amber bottle at 4° C. in a dark place. The stabilized formulation is ready to be conveniently utilized in a peroxidase enzyme assay or enzyme immunoassay as desired.

In a typical enzyme linked immunosorbent assay (ELISA) test, a test sample to be checked for the presence of an antigen is introduced into an assaying environment or microwell containing antibodies specific for the antigen along with antigen-peroxidase conjugate. If the antigen is present in good concentration, it prevents the antigen-peroxidase conjugate from binding to the immobilized antibodies. However, if the antigen is present in low concentration, a greater amount of antigen-peroxidase conjugate is bound to the antibodies.

After a period of incubation, the microwell is washed to remove any unbound antigen-peroxidase conjugate. The colorless substrate formulation containing $H_2O_2$ and the chromatic compound is then added. The test sample and formulation is then examined for the presence or absence of color. Any antigen-peroxidase conjugate bound to the antibodies in the test sample catalyzes the oxidation between $H_2O_2$ and the chromatic compound, resulting in the evolution of a colored product. The optical density of the colored product is measured and compared to calibration tables to determine the extent of peroxidase activity.

DETAILED DESCRIPTION OF THE INVENTION

As indicated above, this invention relates to an innovative and novel stabilized substrate formulation for use in assaying peroxidase activity. The resulting formulation may be stored in solution over long periods of time and provides enhanced color sensitivity for excellent results in the assay procedure.

The formulation is formed of a mixture of two solutions. The first solution includes a chromatic compound. Preferably, the chromatic compound is selected from a group consisting of tetraalkylbenzidine, salts of tetraalkylbenzidine or any mixtures thereof. The most popular chromatic compound is 3,3',5,5'-tetramethylbenzidine (TMB). This compound can be obtained from Aldrich Chemical Company or Sigma Chemical Company.

The TMB is dissolved in a water-miscible organic solvent. While such solvents as dimethyl formamide, dioxane or tetrahydrofuran may be employed, the preferred solvent is dimethyl sulfoxide (DMSO). The TMB is typically dissolved in DMSO at a concentration of between 25 mM and 33 mM.

The second solution includes a stabilizing agent and an acidic buffer substance. The buffer substance may be, for example, chosen from a group consisting of citrate, acetate and phosphate or mixtures thereof. Preferably citrate is used to adjust the pH. When the final formulation is prepared, the pH generally falls within a range between 2.5 and 6.0, and most desirably, between 3.0 and 4.0.

The stabilizing agent used in the invention substrate formulation is bacitracin, such as may be obtained also from Aldrich Chemical Company or Sigma Chemical Company. Since bacitracin is a peptide chain including a series of amino acids, a longer peptide chain including the basic bacitracin constituents (i.e. a bacitracin precursor) may be used. Further, bacitracin components, formed by the breakdown of the parent bacitracin structure into smaller peptide chains and components by hydrolysis, may also be used.

A peroxide for use as an oxidizing agent in the assay reaction is added to the second solution. A liquid peroxide in the form of hydrogen peroxide or a solid peroxide, such as urea hydrogen peroxide, may be used.

The two solutions are prepared at room temperature and mixed together thoroughly. The ratio between the organic solvent and the aqueous buffer solution including the peroxide and stabilizing agent is preferably in the range between 1:99 and 35:65. The formulation is stored in an amber bottle at 4° C. and has been shown to remain stable for a period of several months. The stabilized formulation is ready for use at any time an assay is conducted. The final concentration ranges of the components of the formulation are as follows:

Chromatic compound: 1.0 mM–1.75 mM
Stabilizing agent: 0.5 mM–2.0 mM
Peroxide: 2 mM–10 mM
Buffer: 25 mM–100 mM The following example is presented to illustrate the invention but it is not to be considered as limited thereto.

EXAMPLE

Citric acid monohydrate (3.60 gm) and trisodium citrate dihydrate (1.838 gm) was dissolved in 950 ml of double-distilled water. Bacitracin (1.422 gm) was then added with stirring until it dissolved. Urea hydrogen peroxide (0.564 gm) was added to the above with continuous stirring. 3,3',5,5'-Tetramethylbenzidine (300 mg) was first completely dissolved in 50 ml of dimethyl sulfoxide before adding to the above solution. After thorough mixing in an amber bottle the solution was ready for use or storage at 4° C. The final concentrations of each of the above components was: bacitracin, 1.0 mM; urea hydrogen peroxide, 6 mM; TMB, 1.25 mM; DMSO, 5%; citrate, 25 mM and the final pH was 3.4.

The above substrate solution was examined for its stability at various temperatures. Table I indicates the absorbance reading at 650 nm when the solution was incubated at 4° C., 37° C. or 97° C. for the indicated length of time and then 100 ul of the aliquots were allowed to react with 100 pg of horseradish peroxidase (HRP) at room temperature for 10 min. The absorbance reading was stabilized by adding 100 ul of 1 M phosphoric acid and determined at 450 nm.

TABLE 1

EFFECT OF DIFFERENT TEMPERATURES ON SUBSTRATE STABILITY
(Absorbance at 650 nm after 10 minutes incubation at room temperature)

|  |  | zero time | 30 days | 60 days |
|---|---|---|---|---|
| 4° C. | −HRP | 0.037 | 0.038 | 0.040 |
|  | +HRP | 1.251 | 1.230 | 1.212 |
|  |  | zero time | 5 days | 10 days |
| 37° C. | −HRP | 0.037 | 0.040 | 0.045 |
|  | +HRP | 1.230 | 1.191 | 1.173 |
|  |  | zero time | 2 hours | 4 hours |
| 97° C. | −HRP | 0.037 | 0.041 | 0.046 |
|  | +HRP | 1.470 | 1.405 | 1.005 |

The absorbance values in Table 1 clearly show the excellent color sensitivity of the substrate formulation. With reference to the formulation sample stored at 4° C., there was a significant distinction between readings indicating enzymatic and non-enzymatic activity even after sixty days of storage.

In summary, numerous benefits have been described which result from employing the concept of the present invention. A novel stabilized formulation for use as a substrate in assaying peroxidase activity is disclosed. This formulation includes a chromatic compound such as TMB in solution with $H_2O_2$ and a stabilizing agent from the bacitracin family. The formulation provides for longer storage life for the combination than seen in the prior art. The formulation also enhances the detection sensitivity during the assay procedure.

The invention has been described herein with reference to certain preferred embodiments. However, as obvious variations thereon will become apparent to those skilled in the art, the invention is not to be considered as limited thereto.

I claim:

1. A formulation for the detection and determination of peroxidase activity, comprising:
   a chromatic compound;
   a peroxide;
   a water-miscible organic solvent;
   an aqueous buffer solution; and
   a stabilizing agent selected from a group consisting of bacitracin, bacitracin precursors, bacitracin components derived by hydrolysis and mixtures thereof.

2. The formulation set forth in claim 1 wherein said chromatic compound is selected from a group consisting of tetraalkylbenzidine, salts of tetraalkylbenzidine and mixtures thereof.

3. The formulation set forth in claim 1 wherein said chromatic compound is 3,3',5,5'-tetramethylbenzidine.

4. The formulation set forth in claim 1 wherein said water-miscible organic solvent is selected from a group consisting of dioxane, tetrahydrofuran, dimethyl sulfoxide, dimethyl formamide and mixtures thereof.

5. The formulation set forth in claim 1 wherein said buffer is an acidic buffer selected from a group consisting of citrate, acetate, phosphate and mixtures thereof.

6. The formulation set forth in claim 1 wherein a ratio between said organic solvent and said aqueous solution is between 1:99 and 35:65 volume percent.

7. The formulation set forth in claim 1 wherein a final concentration of said chromatic compound is between 1.0 mM and 1.75 mM.

8. The formulation set forth in claim 1 wherein a final concentration of said peroxide is between 2.0 mM and 10.0 mM.

9. The formulation set forth in claim 1 wherein a final concentration of stabilizing agent is between 0.5 mM and 2.0 mM.

10. The formulation set forth in claim 1 wherein said formulation has a pH between 2.5 and 6.0.

11. A method of assaying peroxidase activity in a test sample using the formulation of claim 1, comprising the steps of:
   introducing said test sample into an assaying environment;
   exposing said test sample to said formulation;
   incubating said test sample and formulation mixture; and
   examining said test sample and formulation mixture for the presence or absence of a colored product.

12. A process for the preparation of a formulation for the detection and determination of peroxidase activity, comprising the steps of:

forming a first solution by dissolving a chromatic compound in a water miscible organic solvent;

forming a second solution by preparing an aqueous acidic buffer solution and adding in any order a stabilizing agent selected from a group consisting of bacitracin, bacitracin precursors, bacitracin components derived by hydrolysis and mixtures thereof and a peroxide; and mixing said first and second solutions to form said formulation.

13. The process of claim 12, wherein said water-miscible organic solvent is selected from a group consisting of dioxane, tetrahydrofuran, dimethyl sulfoxide, dimethyl formamide and mixtures thereof.

14. The process of claim 12, wherein said chromatic compound is selected from a group consisting of tetraalkylbenzidine, salts of tetraalkylbenzidine, and mixtures thereof.

15. The process of claim 12, wherein said chromatic compound is 3,3′, 5,5′-tetramethylbenzidine.

16. The process of claim 12, wherein said aqueous buffer solution is formed using an acidic buffer.

17. The process of claim 16, wherein said acidic buffer is selected from a group consisting of citrate, acetate, phosphate and mixtures thereof.

18. The process of claim 12, wherein a ratio between said first solution and said second solution is between 1:99 and 35:65 volume percent.

19. The process of claim 12, wherein a final concentration of said chromatic compound is between 1.0 mM and 1.75 mM.

20. The process of claim 12, wherein a final concentration of said stabilizing agent is between 0.5 mM and 2 mM.

21. The process of claim 12, wherein a final concentration of said peroxide is between 2.0 mM and 10.0 mM.

22. The process as in claim 12, wherein said formulation has a pH of between 2.5 and 6.0.

* * * * *